United States Patent [19]
Caplan et al.

[11] Patent Number: 4,609,551
[45] Date of Patent: Sep. 2, 1986

[54] PROCESS OF AND MATERIAL FOR STIMULATING GROWTH OF CARTILAGE AND BONY TISSUE AT ANATOMICAL SITES

[76] Inventors: Arnold Caplan, 1300 Oakridge Dr., Cleveland Heights, Ohio 44121; Glenn T. Syftestad, 3660 Warrensville Center Rd. #101, Shaker Heights, Ohio 44122

[21] Appl. No.: 591,440

[22] Filed: Mar. 20, 1984

[51] Int. Cl.$^4$ ............................ A61K 35/32; A61F 2/28
[52] U.S. Cl. ........................................ 424/95; 435/240; 435/241; 514/2; 623/16; 623/66
[58] Field of Search ................. 435/240, 241; 424/95; 514/2; 1,6,17/17

[56] References Cited

U.S. PATENT DOCUMENTS 4,294,753 10/1981 Urist .................................... 424/95
4,456,687 6/1984 Green .................................... 435/2

Primary Examiner—Sam Rosen
Attorney, Agent, or Firm—Watts, Hoffmann, Fisher & Heinke

[57] ABSTRACT

A process for exposing live cells to a soluble bone protein and transferring the cells into appropriate skeletal sites to initiate or enhance local chondrogenesis or osteogenesis. Isogenic fibroblasts are exposed in vitro to a soluble bone protein capable of stimulating in vitro and/or in vivo a chondrogenic response. The fibroblasts are then transferred in vivo in a manner effective to prevent diffusion away from the implantation site so that the desired chondro/osteogenesis reaction can proceed. Delivery systems include: combining the activated fibroblasts with a biodegradable matrix; suspending the activated fibroblasts in a solution suitable for intra-articular injection; and attaching the fibroblasts to allografts and prosthetic devices.

17 Claims, No Drawings

PROCESS OF AND MATERIAL FOR STIMULATING GROWTH OF CARTILAGE AND BONY TISSUE AT ANATOMICAL SITES

DESCRIPTION

1. Technical Field

The present invention relates to a process of and materials for stimulating growth of cartilage and bony tissue, and more specifically to a process wherein cell populations are exposed in vitro to a soluble bone protein and the resultant cells are then delivered in vivo to a selected anatomical site in order to promote chondro/osteogenesis.

2. Background Art

Regeneration of skeletal tissues is regulated by specific protein factors that are naturally present within bone matrix. During the healing process, these components stimulate certain cell populations to form new cartilage and bone tissue which serves to replace that which was lost or damaged. Such protein substances, if extracted and purified, have potential use in clinical situations where skeletal tissue regeneration is necessary to restore normal function, for example, at fracture sites and at sites of periodontal defects. In addition, bony ingrowth into various prosthetic devices can be greatly enhanced so that such artifical parts are firmly and permanently anchored into the surrounding skeletal tissue through a natural osseous bridge. These purified bone proteins are soluble in body fluids and therefore must be presented to the desired wound site through cell delivery, substrate immobilization or surface coating techniques.

DISCLOSURE OF THE INVENTION

This application is related to copending application Ser No. 591,505 which discloses a process of obtaining soluble, purified bone protein capable of causing undifferentiated cells to differentiate, and to copending application Ser. No. 628,168, which discloses processes and techniques for delivering the purified bone protein to anatomical sites. The disclosures of both of said copending applications are incorporated herein by reference.

The present invention is in part based on the discovery that fibroblast-like cells obtained from normal skin tissue can be used to transport the purified bone protein disclosed in Ser. No. 591,505 or the fibroblasts themselves may respond to the protein by forming cartilage, a tissue such cells usually never produce. The acquisition of this new potential for chondrogenesis or the ability to bind the protein occurs in vitro following a short period of exposure of fibroblasts to the protein. Full expression of the cartilage phenotype occurs when the treated fibroblasts are placed into the 'living' environment which appears to be more conducive to the chondrogenic process. The cartilage tissue so formed will remain if direct vascular infiltration is prevented. When the latter occurs, endochondral ossification ensues.

The ready availability of fibroblasts and their potential to produce significant quantities of cartilage and bone when exposed to the purified bone protein make possible the use of isogenically derived skin cells to help regenerate missing or damaged skeletal parts in the same animal or person. These cells can be directly transferred into bone defects such as periodontal cavities and can be attached to porous or varigated surfaces of metal or plastic prosthetic devices to enhance bony ingrowth.

The fibroblasts can also be delivered to the site of the defect within an absorbable matrix, such as fibrin.

In accordance with the foregoing, the invention provides a method in which soluble bone protein, preferably extracted by the process disclosed in Ser. No. 591,505, is made suitable for use in stimulating in vivo growth of skeletal tissue by exposing undifferentiated cells to the soluble bone protein that is purified to a state effective to initiate chondrogenesis, and placing the protein-exposed cells in condition for in vivo administration at a selected anatomical site. The soluble bone protein may be effective to initiate chondrogenesis in the fibroblast or the fibroblast may simply serve to bind the protein and immobilize it at the wound site for a sufficient period to initiate chondrogenesis in a responsive cell population.

In one specific embodiment of the invention, the process includes the steps of combining the exposed cells with a biodegradable carrier such as fibrin to form a composite mass and implanting the composite mass at the site.

In another embodiment of the invention, the process includes the steps of combining the exposed cells with a injectable solution and injecting the cells intraarticularly at the site of a joint cavity articular surface defect.

In a further embodiment, the process includes the steps of incubating the exposed cells with an allograft and implanting the allograft at the site of a skeletal defect.

In still another embodiment of the invention, the process includes the steps of incubating the exposed cells with a prosthesis in a solution which promotes cell adhesion to the prosthesis and implanting the prosthesis.

As used in the following description and claims, soluble bone protein shall mean a bone protein made in accordance with the teachings of Ser. No. 591,505 and having a purity at least equal to that of Protein $A_{VI}$.

Other features and a fuller understanding of the invention will be had from the following detailed description of the best modes.

BEST MODES FOR CARRYING OUT THE INVENTION

Bone matrix contains a number of protein factors which influence various aspects of cell behavior (i.e., migration, replication, attachment, etc.). It has been found that a soluble bone protein stimulates embryonic cells in culture, and particularly embryonic limb mesenchyme, to become cartilage. When removed from its native location within bone, this bone protein is very soluble in body fluids. In order to utilize the purified bone protein for purposes of stimulating local cartilage (and bone) formation in animals and humans, it must first be 'immobilized' so as to prevent rapid diffusion away from the implant site which would prevent the necessary time-dependent factor-cell interaction from occurring.

The process of the present invention ensures that the responding cell population is exposed for a sufficient period to successfully initiate the desired chondrogenic reaction. This is accomplished by the use of an in vitro exposure—in vivo transplantation technique. Cell populations are treated with soluble bone protein while maintained in culture where diffusion problems do not exist. Following an appropriate exposure period, the cells from such cultures are transplanted into the donor/host where chondro/osteogenesis will proceed.

Ubiquitously distributed through the adult organism is a class of cells which shares some of the properties of the embryonic limb mesenchyme in that they too can form cartilage if properly stimulated. This class of cells is generally described as "fibroblastic-like" or simply fibroblasts. Fibroblasts are spindle shaped cells which can rapidly replicate and synthesize a fibrous matrix composed of a variety of extracellular matrix molecules including Type I collagen.

Normal skin tissue, both human and animal, is replete with potentially responsive fibroblasts which can be readily harvested from cultures of skin biopsy samples. Skin fibroblasts can be prepared by enzymatic digestion (0.1% trypsin—0.3% collagenase) of the biopsy sample to release individual cells. Skin fibroblasts can also be prepared by explantation of small pieces (approximately 1 mm$^2$) of intact skin wherein the fibroblasts grow out of the explant onto the culture dish. The fibroblast culture is grown in a suitable medium supplemented with 10% fetal calf serum. Commercially available fibroblast growth factor is added to the medium (10 $\mu$g/ml) to promote rapid cell division. Confluent cultures are then trypsinized (0.1%) and replated at high density (approximately $11 \times 10^4$cells./mm$^2$) into new culture vessels. These cultures are exposed for a minimum of 3 days to purified bone protein (5–10 $\mu$g/ml). Although overt signs of chondrogenesis are not observed (as assessed by visual observation of living cultures), this acquired potential or the transfer of this potential is fully expressed upon transfer to the more 'permissive' environment of the living animal. The presence of cartilage and bone deposits are identified histologically.

Various procedures are contemplated by this invention for transferring and immobilizing the exposed fibroblasts at an anatomical defect site. According to one such procedure, the fibroblasts are directly transferred from a culture dish into small bony defects such as periodontal pockets. The skin fibroblasts synthesize an unusually thick extracellular matrix that holds the cell layer together, and that is easily scraped intact from the culture dish for transfer. The matrix layer in which the fibroblasts are embedded prevents migration of the cells away from the implant site, thus confining cartilage (and bone) formation to the implant site. This layer can be transferred intact into a specific site using forceps or by slow injection through a large 14 gauge, bone needle.

Exposed fibroblasts can form or cause to form healthy cartilage tissue at defective articular surfaces where joint function is compromised. A procedure contemplated by the invention comprises injecting the exposed fibroblasts intra-articularly as a thick cell suspension, for example, a solution of $5 \times 10^6$cells/ml in 10% sucrose. The sucrose facilitates rapid sedimentation and attachment of the fibroblasts onto the damaged cartilage surface. Since the joint cavity is avascular, the fibroblasts form cartilage without being replaced by bone, and can improve joint function at surfaces damaged by trauma or disease.

Exposed fibroblasts can augment bony ingrowth into bone allograft materials. Bone allografts are widely used to stimulate osteogenesis in various types of skeletal defects. Incorporating exposed fibroblasts into allografts can substantially enhance osteogenesis and increase the rate of healing. This is accomplished by incubating an allograft for short periods with exposed fibroblasts which attach to the allograft.

Prosthetic devices of metal or plastic, such as hip replacements, function properly only when the union between device and skeletal tissue is complete. The healing time can be reduced by treating prosthetic devices with exposed fibroblasts so as to enhance rapid osteogenesis at the interface between the device and the host bone. To incorporate fibroblasts, the device is treated with cell adhesion factors such as gelatin.

The following examples more fully describe the invention useful for regenerating skeletal tissue by the process of implanting exposed fibroblasts.

EXAMPLE 1

Skin fibroblasts from nine to eleven day white Leghorn chick embryos were exposed to soluble bone protein, Protein $^A$VI made according to Ser. No. 591,505, at a concentration of 30 $\mu$g/ml, in vitro for three to five days. The fibroblast cell layers were transplanted to day eight chick chorioallantoic membranes. Seven to nine days after transplantation, samples of the membrane were assessed histologically. Membranes treated with exposed fibroblast layers contained cartilage and bone. Membranes treated with unexposed fibroblast layers produced fibrous tissue only.

EXAMPLE 2

Skin fibroblasts from white leghorn embryos were exposed to soluble bone protein, Protein A$_{VI}$, at a concentration of 30 $\mu$g/ml in vitro for three to five days. The fibroblast cell layers were transplanted to an ectopic sub-cutaneous site on white leghorn chick hatchlings. Ten to thirteen days after transplantation, samples of the ectopic sub-cutaneous sites were assessed histologically. Sites treated with exposed fibroblast layers contained both cartilage and bone. Sites treated with unexposed fibroblast layers contained fibrous tissue only.

EXAMPLE 3

The protein-exposed fibroblasts can also be transferred into small bony defects in a fibrin clot carrier. A fibrin clot is useful in that it can be molded to fit the contours of any small defect, for example, defects up to 2–3 cm$^3$. In this example skin fibroblasts from nine to eleven day white Leghorn chick embryos exposed to Protein A$_{VI}$ at a concentration of 30 $\mu$ml in vitro for three to five days. ($5 \times 10^6$cells/ml) were suspended in 2–3 ml of phosphate buffer (pH 7.4) containing fibrinogen (50 $\mu$g/ml) and thoroughly stirred. To this mixture was added 20 units of thrombin (20 $\mu$l of a 1000 units/ml stock solution) per 50 $\mu$g of fibrinogen present. Within several minutes a clot formed, trapping the cells inside.

EXAMPLE 4

Skin fibroblasts from 250 to 300 gm Fischer rats were exposed to soluble bone protein, A$_{VI}$, at a concentration of 30 $\mu$g/ml in vitro for five days. The fibroblast layer was trypsinized and the released cells were mixed into a fibrin clot. The fibrin clot was implanted into a defect in the illiac crest of adult Fischer rats. This defect was created by removing a standarized section (0.5 cm) of crest bone from the illium using a pair of roungers. Three to four weeks after implantation, the implants were assessed histologically. Defect sites implanted with fibrin clots containing exposed fibroblasts showed increased amounts of cartilage or bone formation compared to the amounts of cartilage or bone formed at defect-sites implanted with fibrin clots containing untreated fibroblasts or with fibrin clots alone.

Modifications of the above invention and materials and procedures employed therein which are obvious to persons of skill in the art are intended to be within the scope of the following claims.

We claim:

1. In a method of stimulating in vivo growth of skeletal tissue the improvement comprising the steps of combining soluble bone protein purified to a state effective to initiate chondrogenesis with fibroblast cells to form a protein-cell combination and placing the protein-cell combination in condition for in vivo administration.

2. The method of claim 1 in which the protein-cell combination is combined with a biodegradable carrier to place it in condition for in vivo administration.

3. The method of claim 1 in which the protein-cell combination is combined with fibrinogen and thrombin to form a fibrin clot in which the protein-cell combination is trapped to place it in condition for in vivo administration.

4. The method of claim 1 in which the protein-cell combination is combined with an injectable solution to place it in condition for in vivo administration.

5. The product produced by the process of claim 1.

6. In a method of stimulating in vivo growth of skeletal tissue the improvement comprising the steps of combining soluble bone protein purified to a state effective to initiate chondrogenesis with fibroblast cells to form a protein-cell combination, and further combining the protein-cell combination with a biodegradable carrier to form a composite mass.

7. The method of claim 6 wherein the biodegradable carrier is fibrin.

8. The product produced by the process of claim 6.

9. In a method of stimulating in vivo growth of skeletal tissue the improvement comprising the steps of combining soluble bone protein purified to a state effective to initiate chondrogenesis with fibroblast cells to form a protein-cell combination, and incubating said protein-cell combination with an allograft.

10. The product produced by the process of claim 9.

11. In a method of stimulating in vivo growth of skeletal tissue the improvement comprising the steps of combining soluble bone protein purified to a state effective to initiate chondrogenesis with fibroblast cells to form a protein-cell combination, and incubating said protein-cell combination with a prosthesis in a solution which promotes cell adhesion to the prosthesis.

12. The product produced by the process of claim 11.

13. A method of stimulating in vivo growth of skeletal tissue at an anatomical site comprising the steps of:
    contacting fibroblast cells with soluble bone protein purified to a state effective to initiate chondrogenesis;
    combining the cells with a biodegradable carrier to form a composite mass; and
    implanting the composite mass at the anatomical site.

14. The method of claim 13 wherein the biodegradable carrier is fibrin.

15. A method of stimulating in vivo growth of skeletal tissue at an anatomical site comprising the steps of:
    contacting fibroblast cells with soluble bone protein purified to a state effective to initiate chondrogenesis;
    incubating said cells with an allograft; and
    implanting the allograft at the anatomical site.

16. A method of stimulating in vivo growth of skeletal tissue at an anatomical site comprising the steps of:
    containing fibroblast cells with soluble bone protein purified to a state effective to initiate chondrogenesis;
    incubating the cells with a prothesis in a solution which promotes cell adhesion to the prosthesis; and
    implanting the prosthesis at the anatomical site.

17. A method of stimulating in vivo growth of skeletal tissue at a site of a joint cavity articular comprising the steps of:
    contacting fibroblast cells with soluble bone protein purified to a state effective to initiate chondrogenesis;
    combining the cells with an injectable solution; and
    injecting the cells intra-articularly.

* * * * *